United States Patent
Fearon et al.

(10) Patent No.: US 8,758,356 B2
(45) Date of Patent: Jun. 24, 2014

(54) METHODS AND APPARATUS FOR PREPARING AN INTERCONDYLAR AREA OF A DISTAL FEMUR

(75) Inventors: Kevin Fearon, Rockaway, NJ (US);
Patrick Napolitano, Rockaway, NJ (US); James Tumer, Mine Hill, NJ (US); John Kuczynski, Hewitt, NJ (US)

(73) Assignee: Arthrex, Inc., Naples, FL (US)

(*) Notice: Subject to any disclaimer, the term of this patent is extended or adjusted under 35 U.S.C. 154(b) by 914 days.

(21) Appl. No.: 12/889,952

(22) Filed: Sep. 24, 2010

(65) Prior Publication Data
US 2012/0078260 A1    Mar. 29, 2012

(51) Int. Cl.
*A61B 17/58* (2006.01)
*A61B 17/60* (2006.01)
*A61F 2/00* (2006.01)

(52) U.S. Cl.
USPC .............................................. 606/89

(58) Field of Classification Search
CPC .......... A61B 17/155; A61B 17/1637–17/1642; A61B 17/1695; A61B 17/1668; A61B 17/1675; A61B 17/17; A61B 17/1717–17/1721; A61B 17/1764
USPC .......................................................... 606/89
See application file for complete search history.

(56) References Cited

U.S. PATENT DOCUMENTS

| | | | |
|---|---|---|---|
| 4,474,177 A | 10/1984 | Whiteside | |
| 4,721,104 A | 1/1988 | Kaufman et al. | |
| 5,312,408 A | 5/1994 | Brown | |
| 5,769,854 A * | 6/1998 | Bastian et al. | 606/88 |
| 5,860,981 A | 1/1999 | Bertin et al. | |
| 5,865,834 A | 2/1999 | McGuire | |
| 6,120,511 A | 9/2000 | Chan | |
| 6,371,986 B1 | 4/2002 | Bagby | |
| 6,503,254 B2 | 1/2003 | Masini | |

FOREIGN PATENT DOCUMENTS

| | | |
|---|---|---|
| EP | 1488747 A2 | 12/2004 |
| WO | 2004/041063 A2 | 5/2004 |

OTHER PUBLICATIONS

Extended European Search Report dated Jan. 11, 2012 for EP Application No. 11250820.5.

* cited by examiner

*Primary Examiner* — Sameh Boles
(74) *Attorney, Agent, or Firm* — Carlson, Gaskey & Olds, P.C.

(57) ABSTRACT

Methods and apparatus provide for modifying an intercondylar notch of a patient's femur, including cutting bone from the intercondylar notch using a hole saw having a hollow cylinder and a circular cutting edge, where the hollow cylinder of the hole saw defines a central longitudinal axis which is oriented with reference to the patient's femur such that the circular cutting edge of the hole saw removes a portion of material from the intercondylar notch of the patient's femur.

16 Claims, 11 Drawing Sheets

FIG. 1

(Prior Art)

METHODS AND APPARATUS FOR PREPARING AN INTERCONDYLAR AREA OF A DISTAL FEMUR

BACKGROUND OF THE INVENTION

The present invention relates to methods and apparatus for modifying an intercondylar area of a patient's femur in order to prepare same for receiving a knee prosthesis.

There are a number of different categories of prosthetic knee systems that are used in total knee replacement surgery. Among these categories is the posteriorly stabilized prosthetic knee system, where the posterior cruciate ligament is either weakened or non-present due to injury or disease, or where the posterior cruciate ligament is sacrificed during the knee replacement procedure itself.

Figure 1:
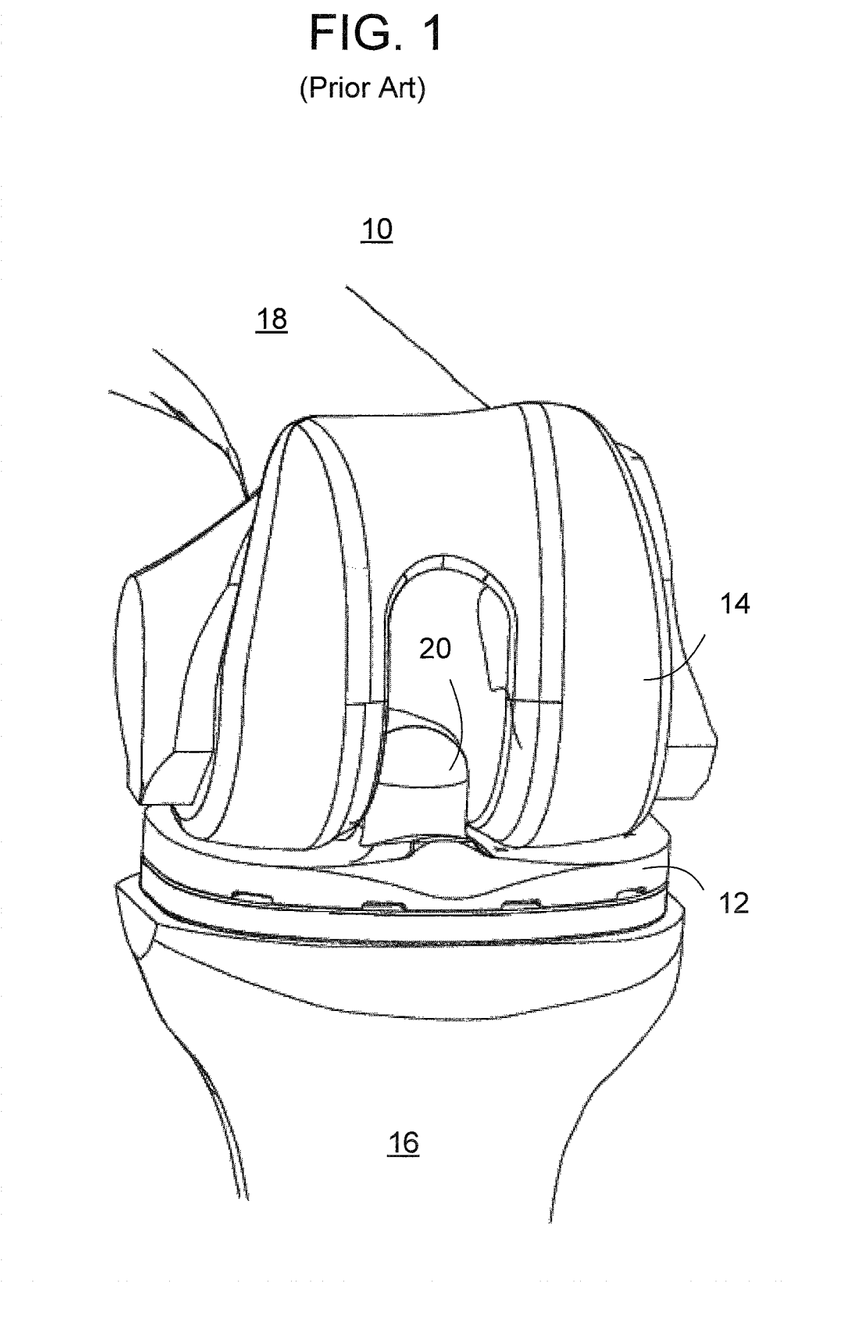
FIG. 1 is a anterior view of a posteriorly stabilized prosthetic knee system in accordance with the prior art.

FIG. 1 illustrates a knee that has been repaired using a known posteriorly stabilized prosthetic knee system 10. The system 10 includes a posteriorly stabilized tibial bearing component 12 and a posteriorly stabilized femoral component 14, which are coupled to the patient's tibia 16 and femur 18, respectively. The femoral component 14 is slotted (including a cam 21, not shown) and the tibial bearing component 12 includes a post 20. The post 20 extends into, and is engaged by, the slot of the femoral component 14 in order to provide both movement and stability of the knee joint.

In order to provide clearance for the cam 21 of the femoral component 14, the post 20 of the tibial bearing component 12, and in some designs a box of the femoral component 14, the intercondylar area of a patient's femur 18 must be modified. Otherwise, the cam 21, post 20, etc. would interfere with the biological structures of the patent's femur 18, and the patient would not enjoy a full range of motion. The bone around the trochlear groove and the intercondylar notch of the distal femur 18 is highly loaded and is, therefore, some of the hardest bone in the body. Some of this very hard bone must be removed in order to provide the aforementioned clearances.

There are a number of known methods to remove the intercondylar bone in preparation for a posteriorly stabilized knee prosthesis system. Perhaps the most common method is to use a notch preparation guide, which includes a series of surfaces to guide a sagittal saw. This technique for preparing the intercondylar notch is described in U.S. Pat. No. 6,503,254, the entire disclosure of which is hereby incorporated herein by reference. The surfaces of the notch preparation guide permit the use of one or more sagittal saws to form three resections at right angles to each other. The three resections leaves a box-shaped intercondylar region, notably with sharp square corners. These sharp corners lead to concentrated bone stresses and the significant possibility of femoral fracture. In some cases, the corners are overcut, where the saw violates the adjacent resection, leading to a very high stress concentration. This method also leads to an excessive amount of bone being removed from the intercondylar area. The more bone that is removed, however, the more likely it is to: (i) compromise the integrity of the modified structures of the femur, and/or (ii) compromise the recovery of the patient.

Another known technique to remove the intercondylar bone in preparation for a posteriorly stabilized knee prosthesis system is described in U.S. Pat. No. 5,769,854, the entire disclosure of which is hereby incorporated herein by reference. In this technique, a notch preparation guide and a punch are used to remove the intercondylar bone. Using a punch and notch-preparation guide is considered an improvement over the sagittal saw because the shape of the box can be better controlled and it takes less time to use a punch than it does to make three saw cuts. As mentioned above, however, the intercondylar bone is very hard and can be very difficult to punch. More problematically, however, is the fact that the punch may result in small or large cracks in the remaining bone of the distal femur. Such cracks may be apparent at the time of surgery or may represent latent damage. In either case, the punch technique may lead to high stress concentrations (at sharp corners and/or cracks), excessive bone removal, a compromise of the structural integrity of the modified femur, and/or limited recovery of the patient.

Yet another technique for preparing the intercondylar notch to receive a posteriorly stabilized total knee system is described in U.S. Pat. No. 4,721,104, the entire disclosure of which is hereby incorporated herein by reference. This technique calls for a notch preparation guide, which guides an end mill to remove the bone from the intercondylar notch. While using a milling device and a notch preparation guide may provide some improvement in the notch preparation, there is a significant disadvantage. The milling device allows for a powered mill to be used to remove the bone from the intercondylar notch. The milling cutter does not result in one or more discrete pieces of bone that may be readily collected and used for other purposes (such as to fill in the intermedullary hole made for femoral alignment). Rather, the milling device creates a "dust" that is relatively useless.

In view of the above, there are needs in the art for new methods and apparatus for preparing an intercondylar area of a patient's femur in order to receive a knee prosthesis. Among the desired characteristics of such new methods and apparatus are the ability to: (i) yield a modified intercondylar notch that exhibits an arch shape (with no sharp corners) in order to achieve structural strength, (ii) remove a relatively low or minimal amount of bone from the intercondylar notch, and (iii) collect discrete bone (preferably one piece) from the intercondylar notch such that the bone may be used for other purposes during or after the knee replacement surgery.

SUMMARY OF THE INVENTION

In accordance with one or more aspects of the present invention, an apparatus for modifying an intercondylar notch of a patient's femur, includes: a guide operating to engage a distal end of the patient's femur, the guide including: (i) exterior surfaces and interior surfaces spaced apart from one another by a thickness of the guide, (ii) a first of the interior surfaces of the guide operating to engage a first surface at a distal end of a patient's femur produced by a distal resection, the first interior surface defining a normal axis thereto, and (iii) a bore extending from one or more of the exterior surfaces to one or more of the interior surfaces of the guide, the bore having an interior cylindrical surface defining a central longitudinal axis. The apparatus additionally or alternatively includes a hole saw having an arbor coupled to a hub, a hollow cylinder extending from the hub, and a circular cutting edge at a distal end of the hollow cylinder.

The bore of the guide is sized and shaped to slidingly receive the hollow cylinder of the hole saw therein, and the central longitudinal axis of the bore is oriented at an acute angle with reference to the normal axis of the first interior surface of the guide such that the circular cutting edge of the hole saw removes a portion of material from the intercondylar notch of the patient's femur. For example, the acute angle between the central longitudinal axis of the bore and the normal axis of the first interior surface of the guide may be between about 40° and 80°, preferably about 60°. The circular cutting edge of the hole saw may be between about 0.5 and about 1.25 inches in diameter, such as about 0.875 inches. Modifications to the above dimensions may be readily made to accommodate different groups of patients, such as of differing size, age, and/or other metric.

The hole saw may include a collar located proximate to the hub, the collar operating to engage a stop member located at a periphery of the bore such that a depth within which the hole saw engages the bore is limited.

The central longitudinal axis of the bore may be oriented with respect to the normal axis of the first interior surface of the guide such that the circular cutting edge of the hole saw removes a piece of bone of crescent-shaped cross-section. Alternatively or additionally, the central longitudinal axis of the bore may be oriented with respect to the normal axis of the first interior surface of the guide such that the circular cutting edge of the hole saw creates an elongate surface within the intercondylar notch of the patient's femur that exhibits an arch-shaped cross-section. Still further variants may additionally or alternatively include that the elongate surface within the intercondylar notch of the patient's femur defines an interior volume, sized and shaped to receive a post of a posteriorly stabilized tibial bearing component of a total knee replacement prosthesis.

The guide may include first and or second further bores, each extending through the first exterior surface and the first interior surface of the guide, and defining first and/or second further central longitudinal axes extending transversely to the first interior surface of the guide. The first and second further bores may operate to provide respective drilling passages into the medial condyle and lateral condyle, respectively, of the patient's femur. The first and/or second further bores may be positioned through the guide such that drilling into the medial and lateral condyles, respectively, provides a bore for receiving a respective mounting post of a posteriorly stabilized femoral component of a total knee replacement prosthesis.

In accordance with one or more further aspects of the present invention, a method for modifying an intercondylar notch of a patient's femur, may include: performing a distal resection on a distal portion of the patient's femur to produce a first surface defining a normal axis thereto; and cutting bone from the intercondylar notch using a hole saw having a hollow cylinder and a circular cutting edge at a distal end of the hollow cylinder, wherein: the hollow cylinder of the hole saw defines a central longitudinal axis which is oriented at an acute angle with reference to the normal axis of the first surface of patient's femur. Additional details previously described may also be employed in the method.

Other aspects, features, and advantages of the present invention will be apparent to one skilled in the art from the description herein taken in conjunction with the accompanying drawings.

DESCRIPTION OF THE DRAWINGS

For the purposes of illustration, there are forms shown in the drawings that are presently preferred, it being understood, however, that the invention is not limited to the precise arrangements and instrumentalities shown.

DETAILED DESCRIPTION OF THE PREFERRED EMBODIMENTS

Figures 2A, 2B:
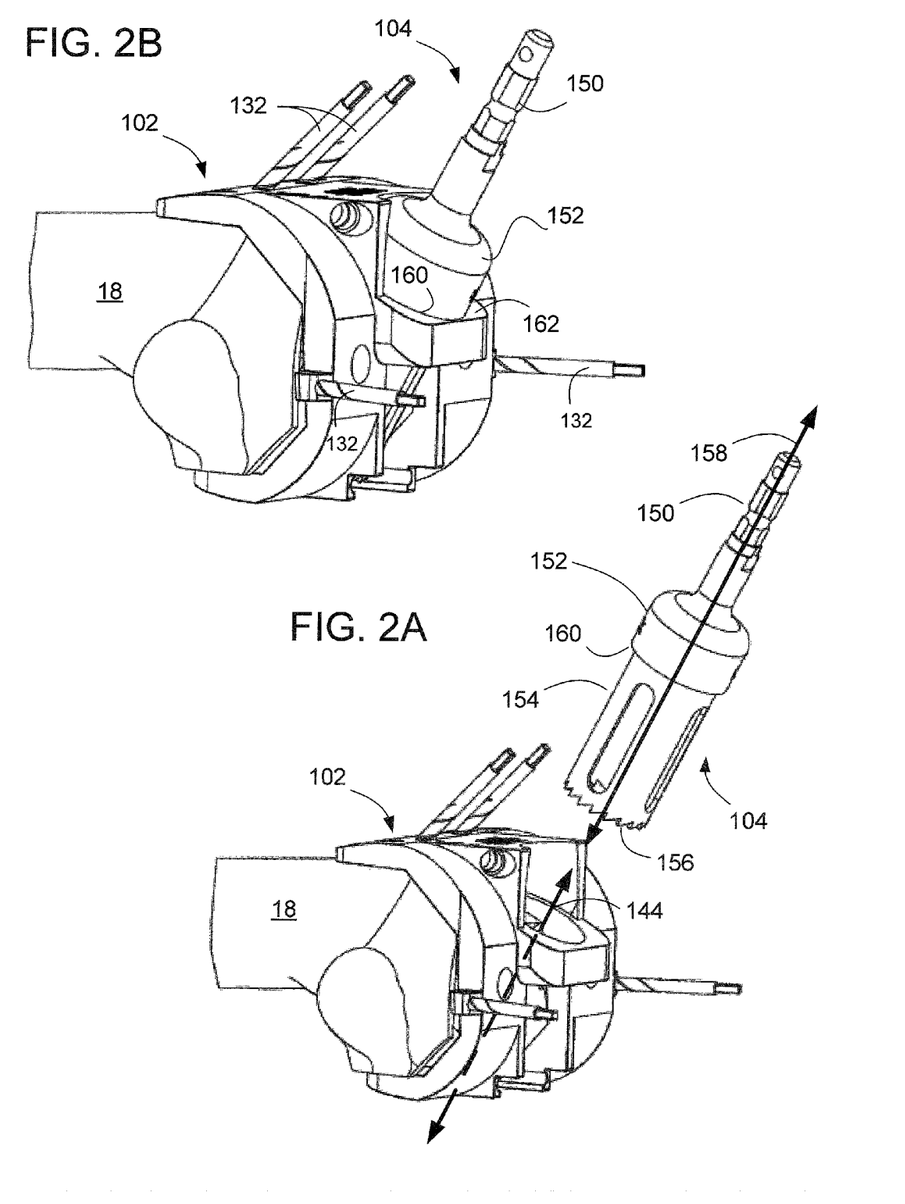
FIGS. 2A and 2B illustrate perspective views of an intercondylar modification system in accordance with one or more embodiments of the present invention.

With reference to the drawings, wherein like numerals indicate like elements, there is shown in FIGS. 2A and 2B a system 100 for modifying the intercondylar notch of a patient's femur 18. The system includes a guide 102 and a hole saw 104. The guide 102 is sized and shaped to firmly engage the distal end of the patient's femur 18 and to provide a well defined orientation of the hole saw 104 such that a cutting edge of the hole saw 104 removes a desired portion of material from the intercondylar notch. As will be discussed in more detail below, the defined orientation and structural characteristics of the hole saw 104, vis-à-vis the guide 102, removes the material from the intercondylar notch of a patient's femur 18 in such a way as to create clearance for certain structural features of a knee prosthesis, such as a posteriorly stabilized prosthetic knee system for total knee replacement. As discussed previously, these structures may include one or more of the cam 21 of the femoral component 14, the post 20 of the tibial bearing component 12, etc., in order to permit a full range of motion.

In one or more embodiments, the guide 104 may share some common features with the femoral component 14 of the posteriorly stabilized prosthetic knee system. For example, the guide 104 may be designed to engage a modified distal femur 18, which has been at least partially resected to receive the femoral component 14. It is understood that while it may be desirable to design the guide 102 to engage a resected femur 18, such is not required in all embodiments of the invention. For purposes of discussion, however, a resected femur 18 will be considered in some detail.

Figure 3:
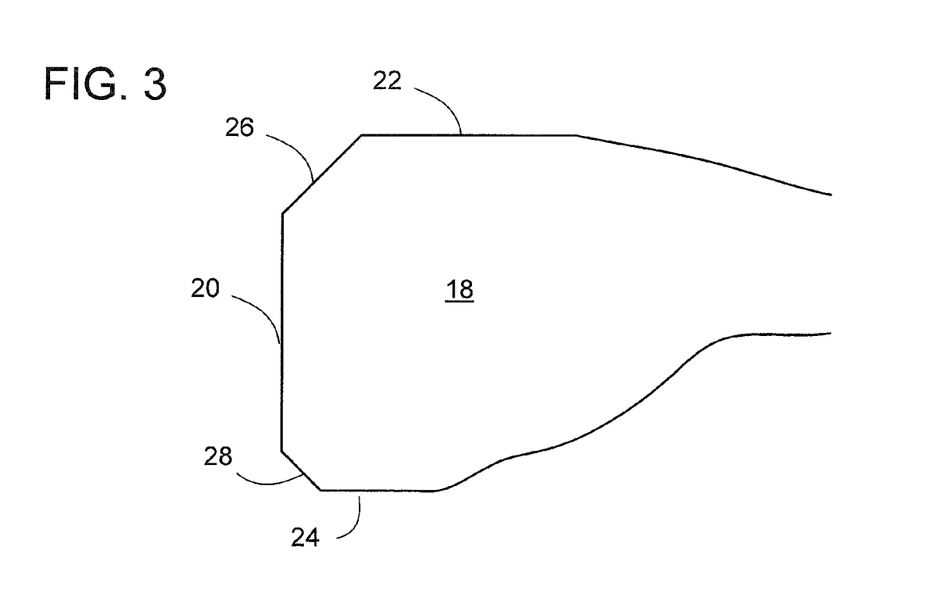
FIG. 3 is a side view of a distal femur that has been resected to receive a posteriorly stabilized femoral component of a prosthetic knee system.

With reference to FIG. 3, the distal femur 18 of the patient may be prepared prior to employing the guide 102 and hole saw 104 to modify the intercondylar area. In particular, a number of resections may be made on the patient's distal femur 18, such as a distal resection (creating a distal resection surface 20), an anterior resection (creating a anterior resection surface 22), and a posterior resection (creating a posterior resection surface 24). Additional resections may also be made to produce a beveled anterior surface 26 between the anterior and distal resection surfaces 20, 22, as well as a beveled posterior surface 28 between the distal and posterior resection surfaces 20, 24.

A number of known surgical procedures are available to surgeons that will enable them to produce the aforementioned resections. Various posterior-stabilized knee prosthesis manufacturers publish procedures for use by surgeons in implanting their prostheses, such as by Howmedica, Inc. and Zimmer USA, Inc. For the purposes of discussion, an acceptable surgical procedure to create the resections may be found in U.S. Pat. No. 4,474,177, which is hereby incorporated herein in its entirety. It is understood, however, that the particular procedure for producing the resections is not intended to limit the scope of the inventive embodiments herein.

Figure 4:
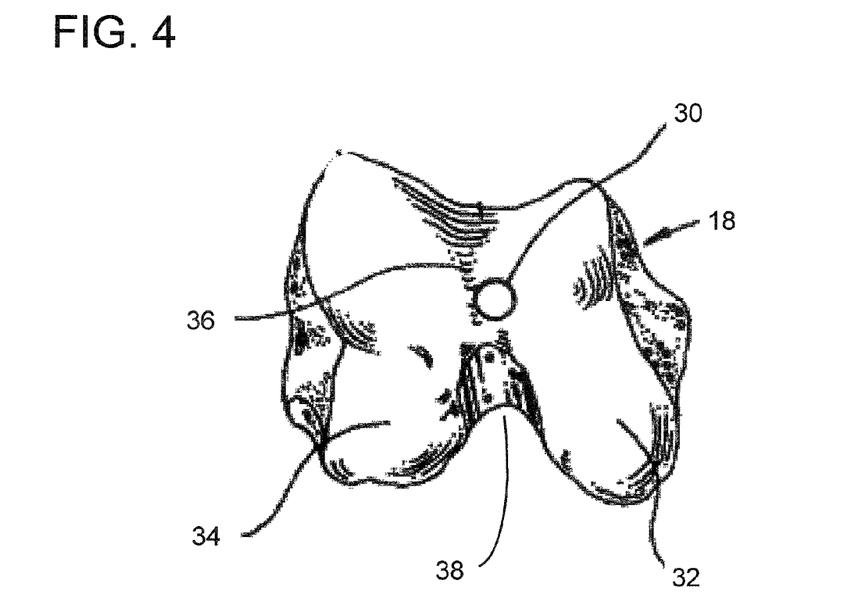
FIG. 4 is a distal view of a distal femur that has been partially modified in preparation for resection.

With reference to FIG. 4, the right distal femur 18 is shown stripped of all other anatomical structures normally present for purposes of clarity. The femur 18 includes a medial condyle 32, a lateral condyle 34, an intercondylar groove 36, and the intercondylar notch (or area) 38. A longitudinally directed bore 30 (directed into the page as illustrated) is drilled into the spongy portion of the femur 18 in order to receive a mounting shaft of a cutting guide apparatus. The cutting guide apparatus includes an anterior-posterior cutting guide, a distal femoral condyle cutting guide, a plateau planer, and a bevel cutting guide. Each of these guides is used to enable the proper orientation of an associated saw to remove bone and other material in order to produce the aforementioned distal resection surface 20, anterior resection surface 22, posterior resection surface 24, beveled anterior surface 26, and beveled posterior surface 28. At this point, the distal femur 18 appears as in FIG. 3 and is ready to receive the guide 102 of the instrument system 100.

Figure 5A:
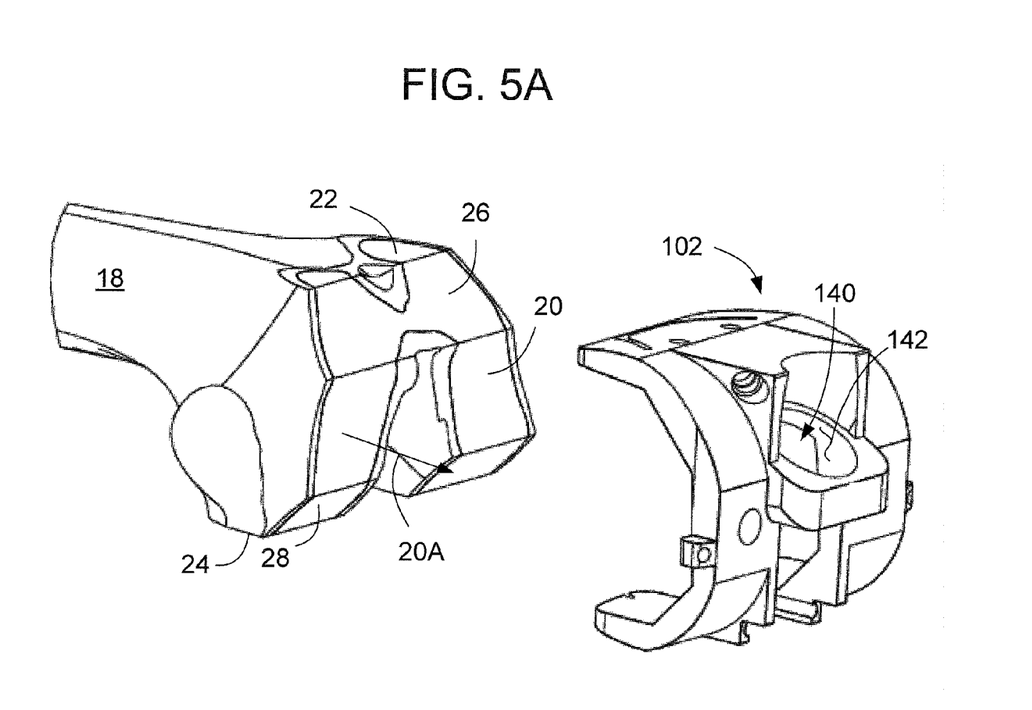
FIGS. 5A and 5B illustrate perspective views of an a guide component of the intercondylar modification system being fitted to a distal femur in accordance with one or more embodiments of the present invention.
Figure 5B:
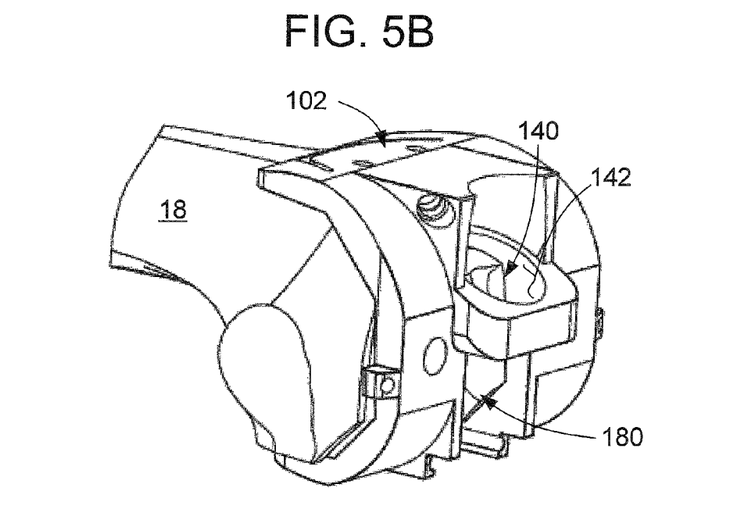

As best seen in FIGS. 5A and 5B, the guide 102 is sized and shaped to engage the distal end of the patient's femur 18, preferably a modified distal femur as discussed above. The guide 102 is preferably shaped to mimic (correspond to) an outer perimeter of the posteriorly stabilized femoral component 14. The guide 102 is also shaped such that it may be utilized with either the right or left femur 18 without modification.

Figure 6A:
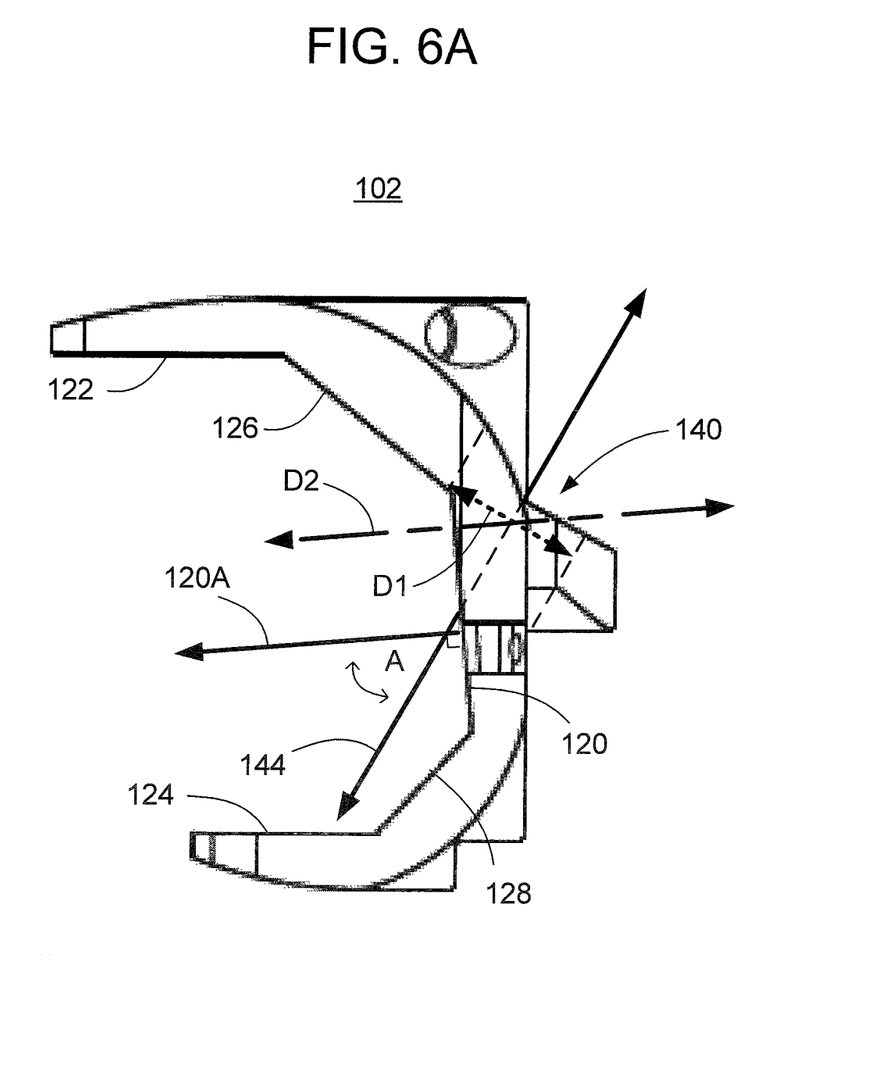
FIG. 6A is a side view of the guide component of the intercondylar modification system in accordance with one or more embodiments of the present invention.
Figure 6B:
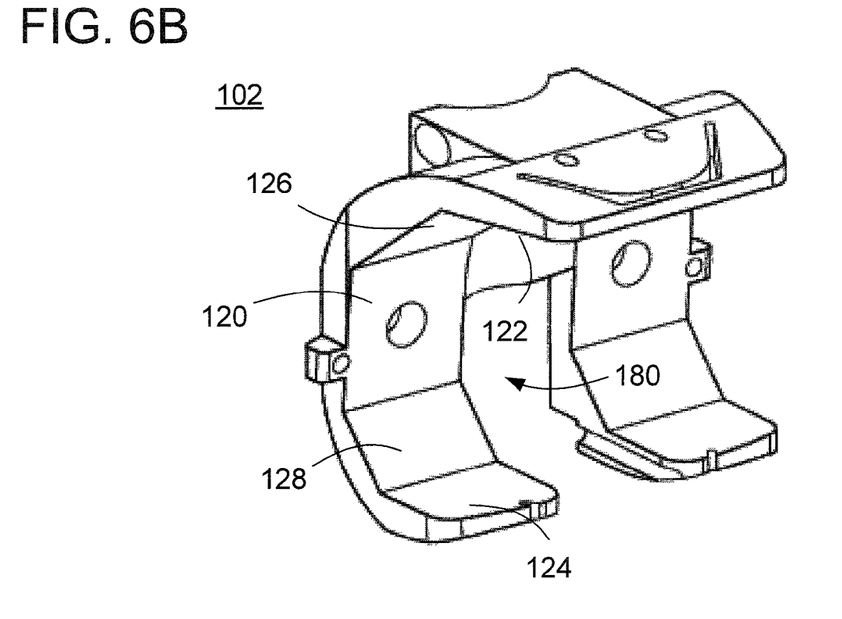
FIGS. 6B and 6C are perspective posterior and anterior views of the guide component of FIG. 6A.

With further reference to FIGS. 6A and 6B, the guide includes exterior surface(s) and interior surface(s) spaced apart from one another by a thickness of the guide 102. The interior surfaces (which may be considered a single surface with separate areas, or a number of separate surfaces) include: a distal engagement surface 120 operating to engage the distal resection surface 20 of the femur 18, an anterior engagement surface 122 operating to engage the anterior resection surface of the femur 18, and a posterior engagement surface 124 operating to engage the posterior resection surface 24 of the femur 18. The interior surfaces may also include a beveled anterior engagement surface 126 operating to engage the beveled anterior surface 26 of the distal femur 18, and a beveled posterior engagement surface 128 operating to engage the beveled posterior surface 28 of the distal femur 18.

Figure 6C:
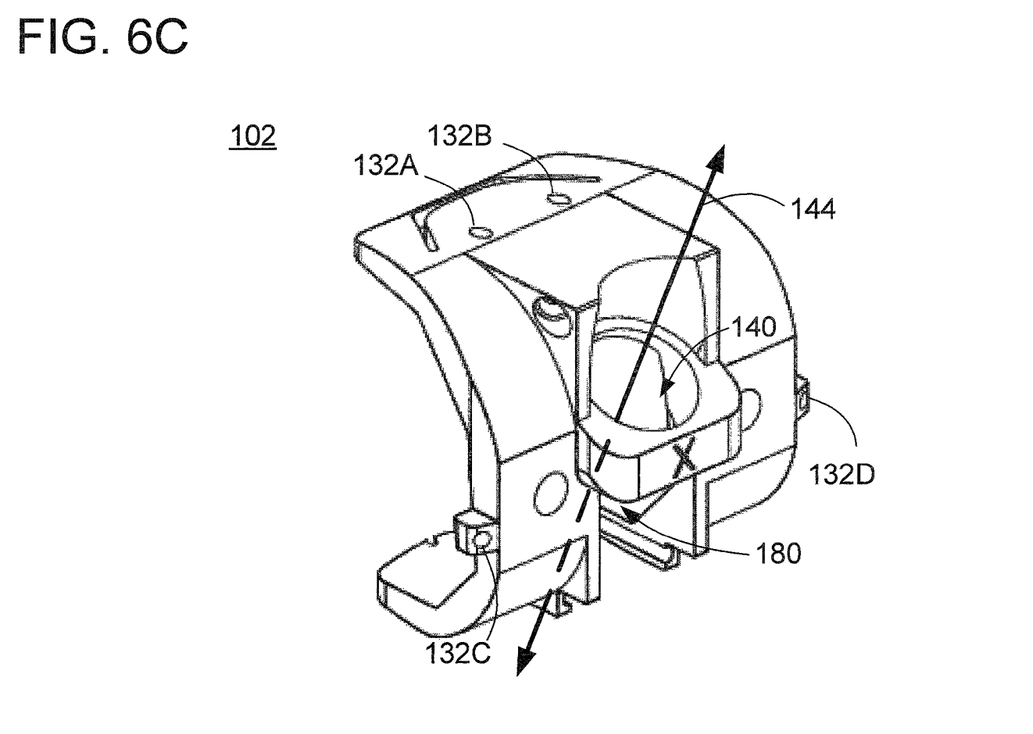

In order to properly locate the guide 102 on the resected femur 18, a "window" feature 180 is included through the outer (anterior) surface of the guide 102 to the interior, which provides a visual indicator of the final femoral component 14 position. By utilizing the outer edge(s) (periphery) of the guide 102 in conjunction with the "window" 180, the surgeon has an accurate indication of implant position (and thus guide 102 position) prior to intercondylar notch preparation/modification. As may be seen in FIG. 6C, the guide 102 includes a number of apertures 130A, 130B, 130C, and 130D (other numbers being feasible). The apertures 130 are positioned such that corresponding fixation pins (threaded or otherwise) may be inserted through the apertures 130 and fix the guide 102 to the distal femur 18. Any of the known and readily available fixation pins 132 may be employed for this purpose. The guide fixed to the femur 18 via the fixation pins 132 may be seen in FIGS. 2A and 2B.

As may be seen in any number of views, the guide 102 includes a bore 140 extending from one or more of the exterior surfaces to one or more of the interior surfaces of the guide 102. The bore 140 includes an interior surface 142 defining a central longitudinal axis 144. When the bore 140 is of circular cross-section, the interior surface 142 is cylindrical. Those skilled in the art will appreciate that the bore 140 may be of any suitable configuration, such as circular, rectangular, triangular, oval, etc. The central longitudinal axis 144 of the bore 140 is oriented such that the hole saw 104 is correspondingly oriented such that a cutting edge of the hole saw 104 removes a desired portion of material from the intercondylar notch.

For example, the central longitudinal axis of the bore 140 may be oriented at an angle with reference to an anatomical reference plane or axis of the patient. Such anatomical reference plane may be one or more of a sagittal plane, a coronal plane, and/or a transverse plane of the patient. Preferably, the anatomical reference is with respect to the distal engagement surface 120 of the guide 102. Thus, the central longitudinal axis 144 of the bore 140 may be oriented at an angle with reference to the distal engagement surface 120 of the guide 102. In particular, and with reference to FIGS. 3 and 6A, the distal resection surface of the femur 18 defines a normal axis 20A (FIG. 5A), and the distal engagement surface 120 of the guide 102 also defines a normal axis 120A. The normal axes 20A and 120A are coaxial (or at least parallel) when the guide 102 is fixed in place on the femur 18. As best seen in FIG. 6A, the central longitudinal axis 144 of the bore 140 is oriented at an acute angle A with reference to normal axes 20A and 120A of the distal resection surface 20 and the distal engagement surface 120, respectively.

Although aspects of the invention are not limited by any particular theory of operation, it has been found that desirable characteristics of the modified intercondylar area are achieved when the acute angle between the central longitudinal axis 144 of the bore 140 and the normal axes 20A and/or 120A is between about 0° and 90°, for example, about 60°.

With reference to FIGS. 2A and 2B, the hole saw 104 includes an arbor 150 (for engagement with a driving mechanism, such as a motorized drill) coupled to a hub 152. A hollow cylinder 154 extends from the hub 152, and includes a circular cutting edge 156 at a distal end thereof. The bore 140 of the guide 102 is sized and shaped to slidingly receive the hollow cylinder 154 of the hole saw 104 therein, and to orient a central longitudinal axis 158 of the hole saw 104 to be coaxial with the central longitudinal axis 144 of the bore 140. In this orientation, the hole saw 104 is rotated at a sufficient speed (via the drill) and pressed through the bore 140 of the guide 102 until engagement is made between the cutting edge 156 and the material (bone, cartilage, etc.) of the intercondylar area. Continued pressure is applied to drive the hole saw 104 further through the bore 140 (maintaining the axial relationship between the axes 144 and 156) such that the circular cutting edge 156 of the hole saw 104 removes a desired portion of material from the intercondylar notch of the patient's femur 18.

In order to control how far the hole saw 104 is driven into the bore 140, the hole saw 104 may include a collar 160 located proximate to the hub 152, where the collar 160 operates to engage a stop member 162 located at a periphery of the bore 140. In such a configuration, a depth within which the hole saw 104 engages the bore 140 is limited. Alternatively or additionally, the depth limiting feature may include indicia located on the hole saw 104 (such as a circumferential line), which with reference to one or more structures of the guide 102 (such as the periphery of the bore 140) provides a visual indication as to a desired depth within which the hole saw 104 engages the bore 140.

Figure 7A:
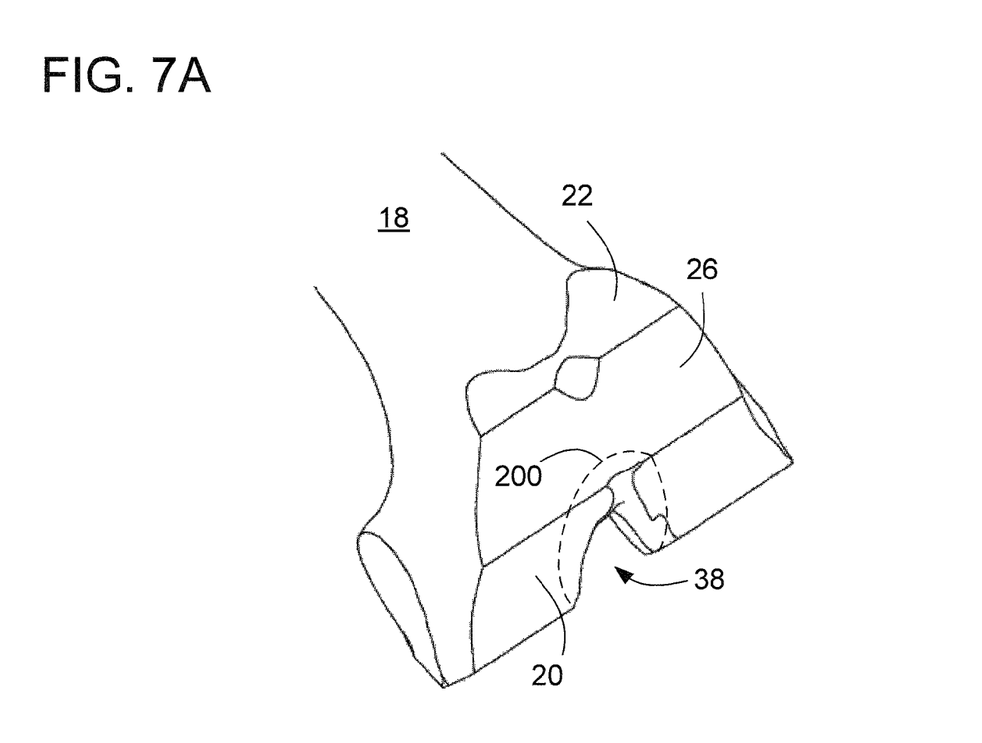
FIG. 7A is a perspective view of a distal femur that has been resected but without modification to the intercondylar notch.
Figure 7B:
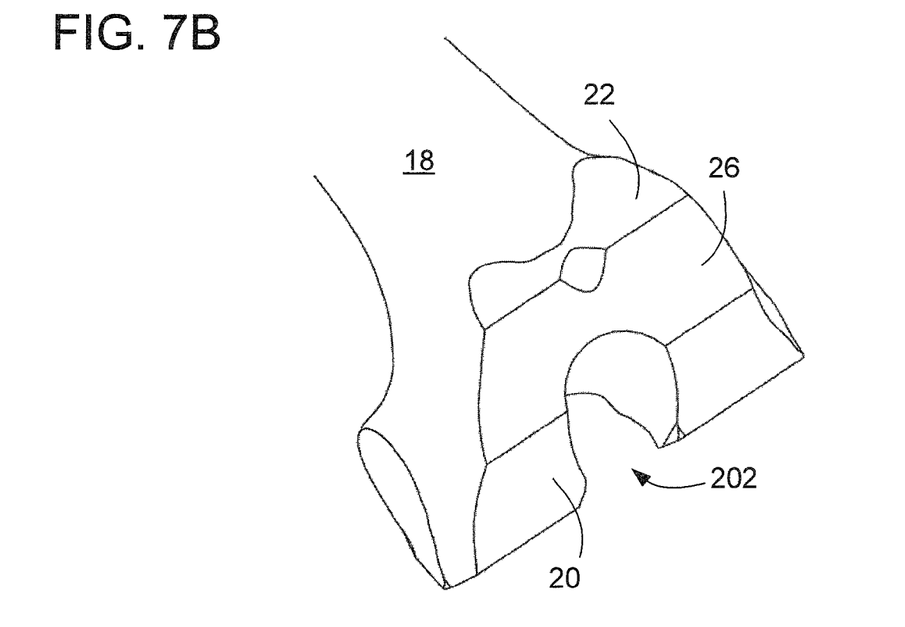
FIG. 7B is a perspective view of the distal femur of FIG. 7A that has been modified using the intercondylar modification system in accordance with one or more embodiments of the present invention.

With reference to FIGS. 7A and 7B, the above process and structural characteristics of the guide 102 and hole saw 104 removes a piece of bone of crescent-shaped 200 cross-section from the intercondylar notch 38 of the distal femur 18. This removal of material creates an elongate surface within the intercondylar notch of the patient's femur that exhibits an arch-shaped 202 cross-section.

Figure 8:
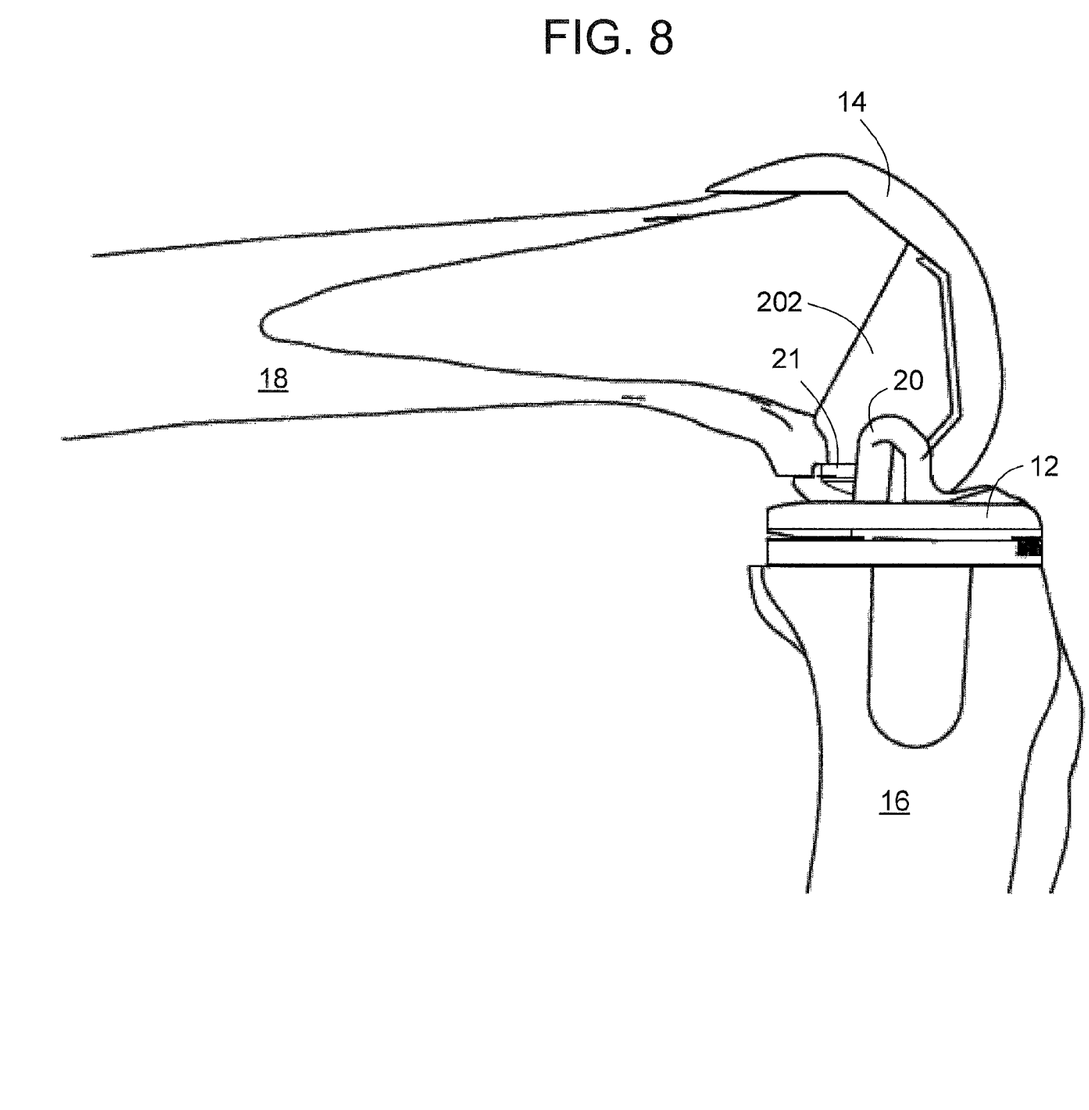
FIG. 8 is a side, partially cross-sectional view of the distal femur that has been modified using the intercondylar modification system and that has been fitted with a posteriorly stabilized prosthetic knee system.

With reference to FIG. 8, the guide 102 is removed from the femur 18, the posteriorly stabilized tibial bearing component 12 is fixed to the tibia 16, and the posteriorly stabilized femoral component 14 is coupled to the femur 18. The elongate surface 202 within the intercondylar notch of the patient's femur 18 defines an interior volume, sized and shaped to receive the post 20 of the posteriorly stabilized tibial bearing component 12 and provide enough clearance to permit a full range of motion of the prosthetic.

It is noted that variation in the characteristics of the removed material 200 (and thus the shape of the remaining surface(s) 202 of the intercondylar area of the femur 18) may be obtained through modifications to the diameter (or radius) of the cutting edge 156 of the hole saw 104. While the diameter may be of any suitable value, it has been determined that desirable results should be obtained in a large number of patients when the circular cutting edge 156 of the hole saw 104 is between about 0.500 and about 1.250 inches in diameter, such as about 0.875 inches.

With reference to FIG. 6A, it is noted that additional variation in the characteristics of the removed material 200 (and thus the shape of the remaining surface(s) 202 of the intercondylar area of the femur 18) may be obtained through modifications to the orientation of the central longitudinal axis 144 of the bore 140 (with or without modifying the acute angle A and/or the diameter of the hole saw 104). In particular, an amount and/or character of the removed material 200 may be achieved by modifying a "depth" of cut with respect to the longitudinal dimension of the femur 18. Such modification to the depth of cut may be achieved in any number of ways, such as by locating the bore 140 such that the central longitudinal axis 144 lies in a different position along line D1. Moving the central longitudinal axis 144 closer to the intercondylar notch along line D1 will remove more material 200, while moving the central longitudinal axis 144 further from the intercondylar notch along line D1 will remove less material 200. Additionally or alternatively, modification to the depth of cut may be achieved by locating the bore 140 such that the central longitudinal axis 144 lies in a different position along line D2 (which may run parallel to the normal axis 120A). Moving the central longitudinal axis 144 closer to the intercondylar notch along line D2 will remove more material 200, while moving the central longitudinal axis 144 further from the intercondylar notch along line D2 will remove less material 200.

The above discussion has been focused on describing and defining aspects of the inventive concepts with regard to the angle A formed between the central longitudinal axis 144 of the bore 140 and the normal axes 20A and 120A of the distal resection surface 20 and the distal engagement surface 120, respectively. It is noted, however, that the aspects of the invention may be readily described and defined in terms of alternative geometries that are inherently related to the aforementioned geometries. For example, aspects of the invention may be readily described and defined in terms of the angle(s) formed between the central longitudinal axis 144 of the bore 140 and normal axes (or other definable axes) of the distal engagement surface 120, the distal resection surface 20, the anterior engagement surface 122, the anterior resection surface 22, the posterior engagement surface 124, the posterior resection surface 24, the beveled anterior engagement surface 126, the beveled anterior surface 26, the beveled posterior engagement surface 128, and/or the beveled posterior surface 28. Since any of the above geometries may be inherently and easily derived from the detailed description of the interrelationship among the central longitudinal axis 144 and the normal axes 20A and 120A, additional discussion of this topic will be omitted for brevity and clarity.

Figure 9A:
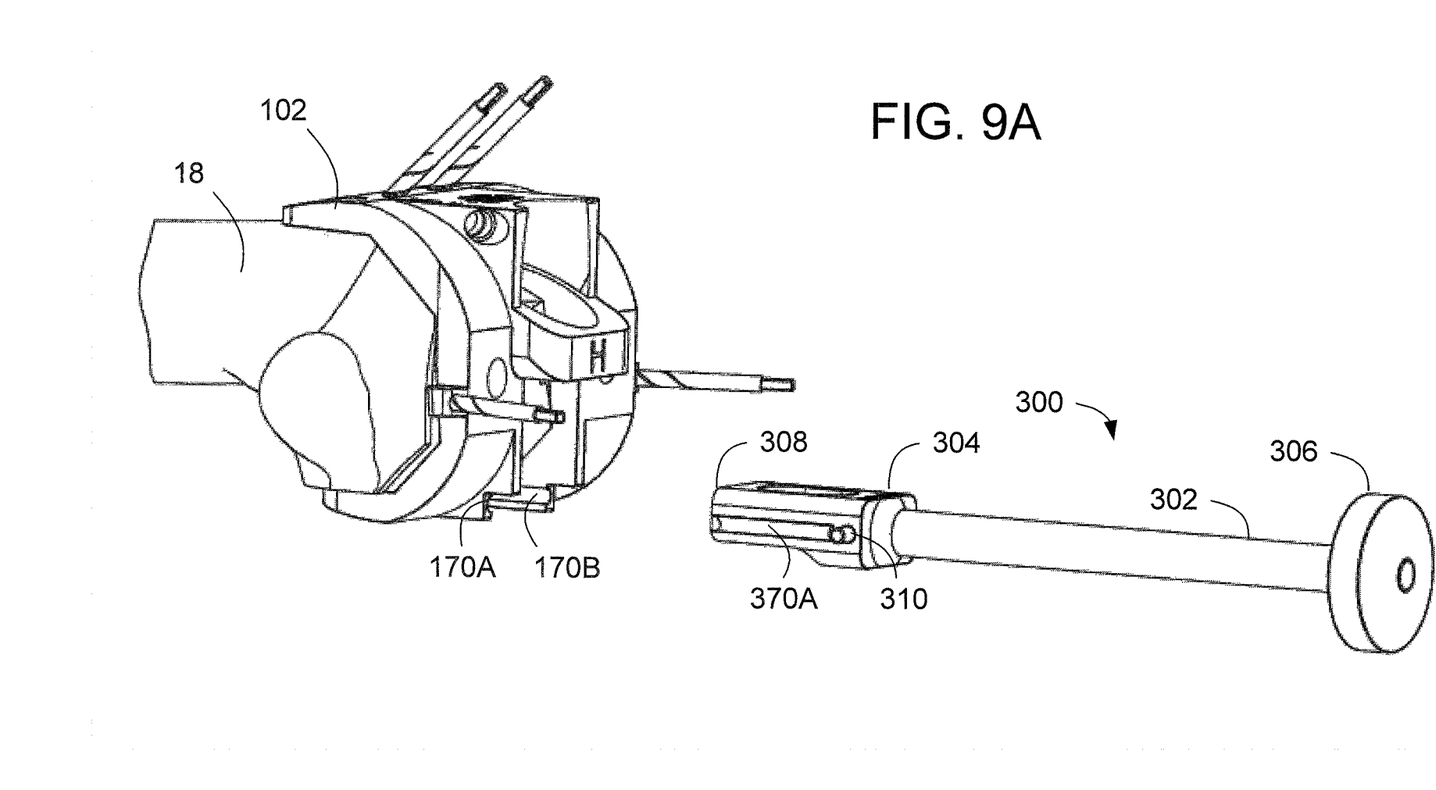
FIGS. 9A and 9B illustrate perspective views of the guide component of the intercondylar modification system being used to further modify the distal femur in accordance with one or more embodiments of the present invention to receive a cam of the femoral component of the posteriorly stabilized prosthetic knee system.
Figure 9B:
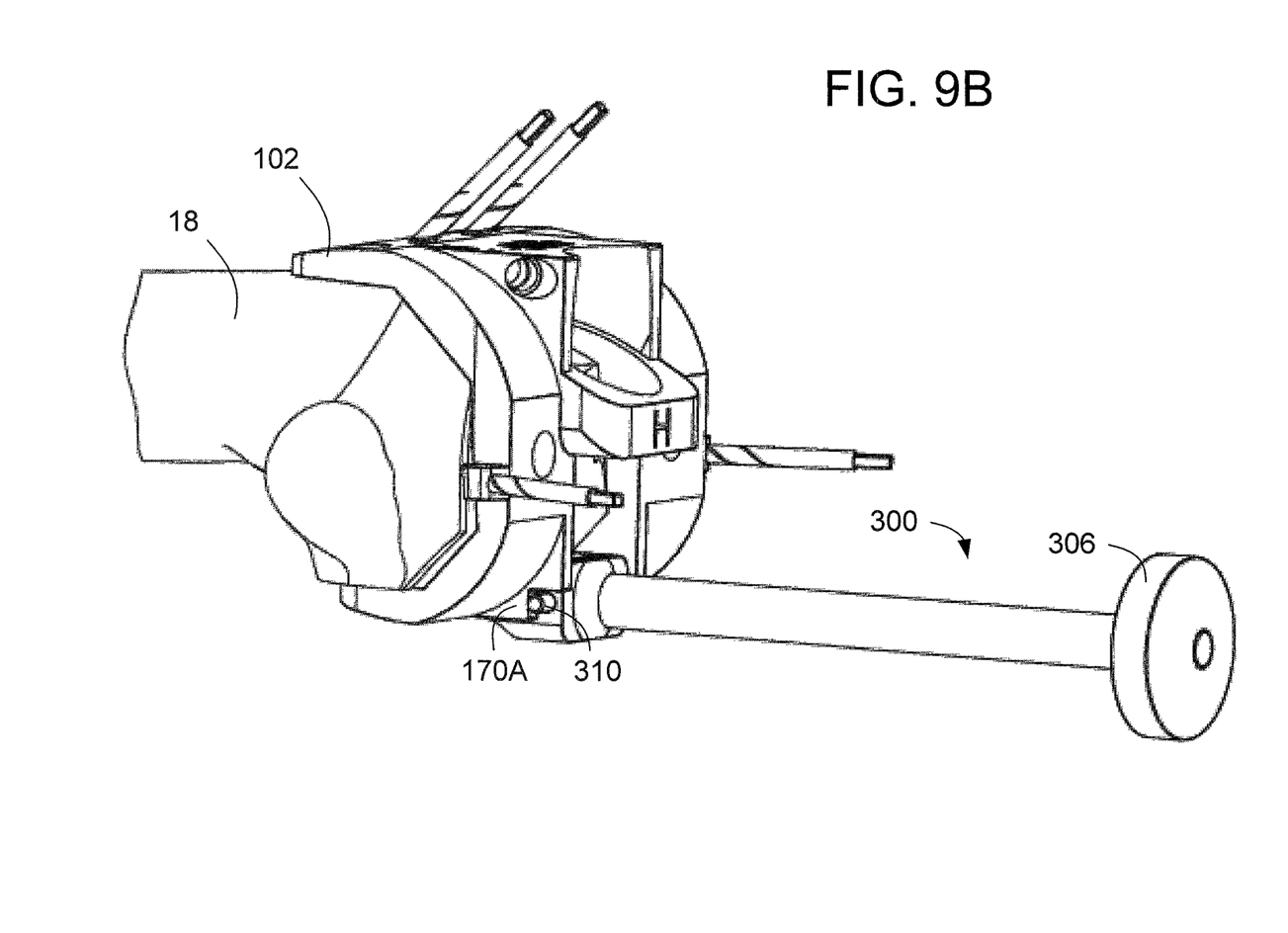

With reference to FIGS. 6D, 6E, 8, 9A, and 9B, the guide 102 may include alterative or additional structural features that achieve further desirable functions. For example, as shown in FIGS. 9A-9B, some posteriorly stabilized femoral components 14 may include some structural element(s) near the cam 21 that require that additional material (bone, etc.) be removed from the intercondylar notch. Accordingly, the guide 102 may include at least a pair of oppositely disposed grooves 170A, 170B that each extend substantially parallel to (and below) the posterior engagement surface 124. The system 100 may further include a tool 300, including a shaft 302, a head 304, and a driver element 306. The head 304 slidingly engages the guide 102 by way of a pair of oppositely disposed protrusions 370A, 370B that engage the grooves 170A, 170B, respectively. The head 304 also includes a partially rectangular peripheral cutting surface 308 (punch) that geometrically complements the shape of the material that must be removed from the intercondylar area to accommodate the cam 21 of the posteriorly stabilized femoral component 14. The head 304 may further include one or more stop elements 310 (preferably one on each side of the head 304) that are located at a proximal end of each protrusion 370. The stop elements 310 engage peripheral portions of the guide 102 proximate to the grooves 170A, 170B to provide a limit to the depth that the head 304 may enter the guide 102 (and this a limit a depth that the punch 308 is permitted to drive into the femur 18). The head 304 is slid into the guide 102, and cutting edge 308 is driven into the femur 18 by way of the driver element 306 to remove the material.

Figure 6D:
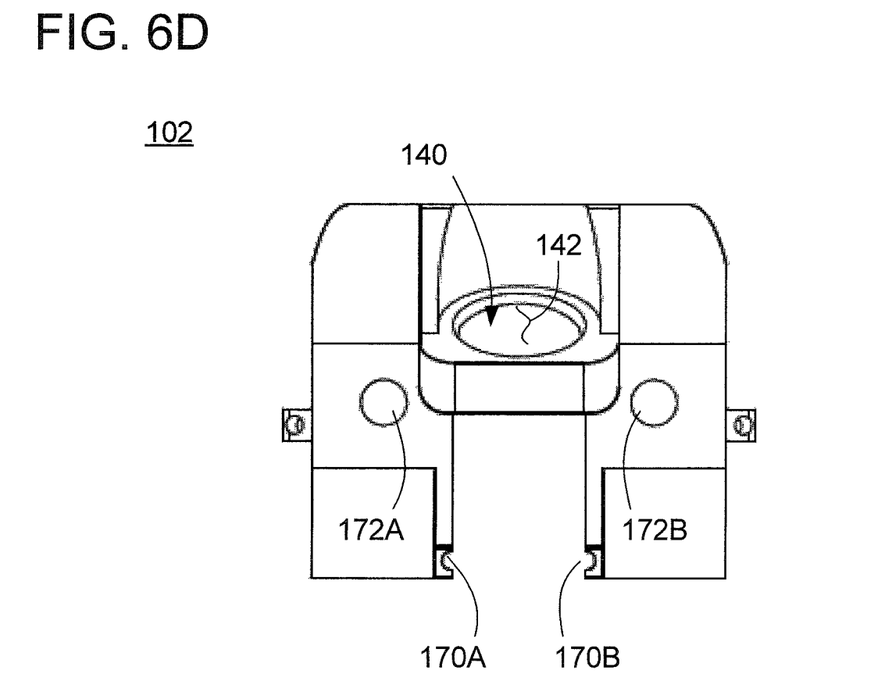
FIGS. 6D and 6E are perspective anterior and posterior views of the guide component of FIG. 6A.
Figure 6E:
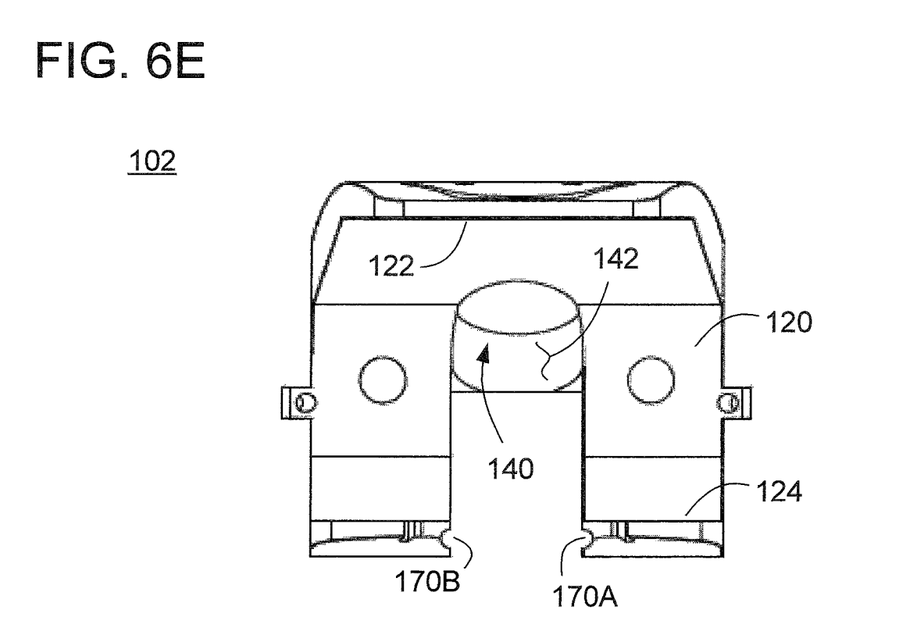

With reference to FIG. 6D, the guide 102 may include alterative or additional structural features that achieve further desirable functions. For example, the guide 102 may include a first further bore 172A extending through the first exterior surface and the first interior surface of the guide 102, thereby defining a first further central longitudinal axis extending transversely to the distal resection surface 120 of the guide 102. The bore 172A provides a drilling passage into a medial condyle 32 of the patient's femur 18 for receiving a corresponding mounting post of the posteriorly stabilized femoral component 14. The guide 102 may additionally or alternatively include a second further bore 172B extending through the first exterior surface and the first interior surface of the guide, and defining a second further central longitudinal axis extending transversely to the distal resection surface 120 of the guide 102. The second bore 172B provides a drilling passage into a lateral condyle 34 of the patient's femur 18 for receiving a corresponding mounting post of the posteriorly stabilized femoral component 14.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An apparatus for modifying an intercondylar notch of a patient's femur, comprising: a guide operating to engage a distal end of the patient's femur, the guide including: (i) exterior surfaces and interior surfaces spaced apart from one another by a thickness of the guide, (ii) one or more mounting elements operating to engage a distal end of the patient's femur and (iii) a bore extending from one or more of the exterior surfaces to one or more of the interior surfaces of the guide, the bore having an interior surface defining a central longitudinal axis; and a hole saw having a hollow cylinder extending from the hub, and a circular cutting edge at a distal end of the hollow cylinder, wherein: the bore of the guide is sized and shaped to slidingly receive the hollow cylinder of the hole saw therein, and the central longitudinal axis of the bore is oriented at an acute angle with reference to a normal axis of the one or more of the interior surfaces of the guide such that the circular cutting edge of the hole saw removes a portion of material from the intercondylar notch of the patient's femur.

2. The apparatus of claim 1, wherein the central longitudinal axis of the bore is oriented at an angle with reference to an anatomical reference plane or axis of the patient.

3. The apparatus of claim 2, wherein the anatomical reference plane is at least one of a sagittal plane, a coronal plane, and a transverse plane of the patient.

4. The apparatus of claim 3, wherein:
the one or more mounting elements include a first of the interior surfaces of the guide operating to engage a first surface at a distal end of the patient's femur produced by a distal resection, the first interior surface defining a normal axis thereto; and
the anatomical reference plane is at least one of the first surface at a distal end of the patient's femur, and the first interior surface of the guide.

5. The apparatus of claim 4, wherein the central longitudinal axis of the bore is oriented at an angle with reference to the normal axis of the first interior surface of the guide such that the circular cutting edge of the hole saw removes the portion of material from the intercondylar notch of the patient's femur.

6. The apparatus of claim 5, wherein the angle between the central longitudinal axis of the bore and the normal axis of the first interior surface of the guide is between about 0° and 90°.

7. The apparatus of claim 6, wherein the angle is about 60°.

8. The apparatus of claim 1, wherein the circular cutting edge of the hole saw is between about 0.5 and about 1.25 inches in diameter.

9. The apparatus of claim 8, wherein the circular cutting edge of the hole saw is about 0.875 inches in diameter.

10. The apparatus of claim 1, wherein the hole saw includes a depth limiting feature such that a depth within which the hole saw engages the bore is limited.

11. The apparatus of claim 10, wherein the depth limiting feature includes a collar located on the hole saw, the collar operating to engage a stop member located at a periphery of the bore such that a depth within which the hole saw engages the bore is limited.

12. The apparatus of claim 10, wherein the depth limiting feature includes indicia located on the hole saw, which with reference to one or more structures of the guide provides a visual indication as to a desired depth within which the hole saw engages the bore.

13. The apparatus of claim 1, wherein the central longitudinal axis of the bore is oriented with respect to the normal axis of the first interior surface of the guide such that the circular cutting edge of the hole saw removes a piece of bone of crescent-shaped cross-section.

14. The apparatus of claim 1, wherein the central longitudinal axis of the bore is oriented with respect to the normal axis of the first interior surface of the guide such that the circular cutting edge of the hole saw creates an elongate surface within the intercondylar notch of the patient's femur that exhibits an arch-shaped cross-section.

15. The apparatus of claim 14, wherein elongate surface within the intercondylar notch of the patient's femur defines an interior volume, sized and shaped to receive a post of a posteriorly stabilized tibial bearing component of a total knee replacement prosthesis.

16. The apparatus of claim 1, wherein the guide includes at least one of:
a first of the exterior surfaces spaced apart from the first interior surface of the guide;
a first further bore extending through the first exterior surface and the first interior surface of the guide, and defining a first further central longitudinal axis extending transversely to the first interior surface of the guide, and operating to provide a drilling passage into a medial condyle of the patient's femur;
a second further bore extending through the first exterior surface and the first interior surface of the guide, and defining a second further central longitudinal axis extending transversely to the first interior surface of the guide, and operating to provide a drilling passage into a lateral condyle of the patient's femur; and
at least one of the first and second further bores are positioned through the guide such that drilling into the medial and lateral condyles, respectively, provides a bore for receiving a respective mounting post of a posteriorly stabilized femoral component of a total knee replacement prosthesis.

* * * * *

UNITED STATES PATENT AND TRADEMARK OFFICE
CERTIFICATE OF CORRECTION

PATENT NO. : 8,758,356 B2  
APPLICATION NO. : 12/889952  
DATED : June 24, 2014  
INVENTOR(S) : Kevin Fearon

Page 1 of 1

It is certified that error appears in the above-identified patent and that said Letters Patent is hereby corrected as shown below:

ON THE TITLE PAGE:

Item 75 Inventor James Turner should read as --James Turner, Mine Hill, NJ (US)--

Signed and Sealed this
Seventh Day of October, 2014

Michelle K. Lee
*Deputy Director of the United States Patent and Trademark Office*